United States Patent [19]

Benzing, III et al.

[11] 4,245,643
[45] Jan. 20, 1981

[54] METHOD AND APPARATUS FOR MEASURING THE OHMIC CONTACT RESISTANCE OF AN ELECTRODE ATTACHED TO BODY TISSUE

[75] Inventors: George Benzing, III; Rumult Iltis, both of Cincinnati, Ohio

[73] Assignee: Children's Hospital Medical Center, Cincinnati, Ohio

[21] Appl. No.: 66,770

[22] Filed: Aug. 15, 1979

[51] Int. Cl.³ .............................................. A61N 1/36
[52] U.S. Cl. .............................................. 128/419 PT
[58] Field of Search ............. 128/419 PT, 419 R, 421, 128/422, 695, 696, 697, 642

[56] References Cited

U.S. PATENT DOCUMENTS

| 3,757,790 | 9/1973 | Herrman | 128/419 PT |
| 3,866,600 | 2/1975 | Rex | 128/422 |
| 4,141,367 | 2/1979 | Ferreira | 128/419 PT |

OTHER PUBLICATIONS

Benzing 3rd et al., "Journal of Biomedical Engineering", vol. 2, No. 1, Jan. 1980, pp. 3–8.

Primary Examiner—William E. Kamm
Attorney, Agent, or Firm—Wood, Herron & Evans

[57] ABSTRACT

A method and apparatus are disclosed for measuring the ohmic, that is, purely d-c, resistance at the area of contact between cardiac tissue and a pacemaker electrode surgically implanted in the heart of a patient requiring a pacemaker. The contact resistance is measured by apparatus connected across the electrical circuit formed by the electrode and heart. The apparatus includes circuitry for sampling and holding the instantaneous voltage across the electrical circuit formed by the electrode and heart at the onset of a pulse generated by the pacemaker pulse generator, at which time the effect of a parallel capacitance in the electrical circuit formed by the pulse generator, electrode wire, electrode, heart, and return path through the body to the pulse generator is such that the current initially produced is determined only by the voltage and equivalent output impedance of the pulse generator, the resistance of the electrode wire, and the resistance at the area of contact between cardiac tissue and the electrode. The apparatus further includes analog signal processing circuitry for deriving the contact resistance from the instantaneous voltage based on an equivalent circuit model for the electrical circuit formed by the pacemaker and the heart taking into account the effect of the parallel capacitance at the onset of a pulse. The apparatus also includes a device for displaying the measured contact resistance. The disclosed method and apparatus are also applicable for measuring the ohmic contact resistance of an electrode attached to other body tissue.

9 Claims, 5 Drawing Figures

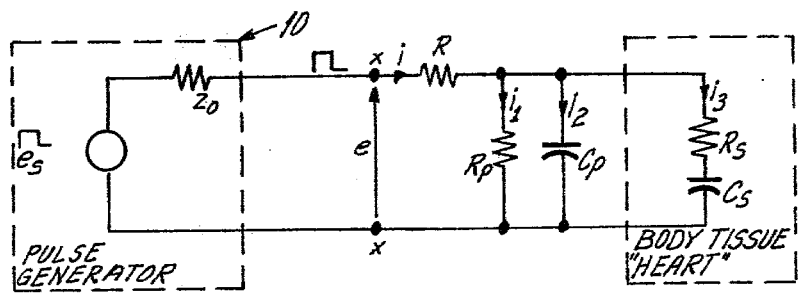
Fig. 1
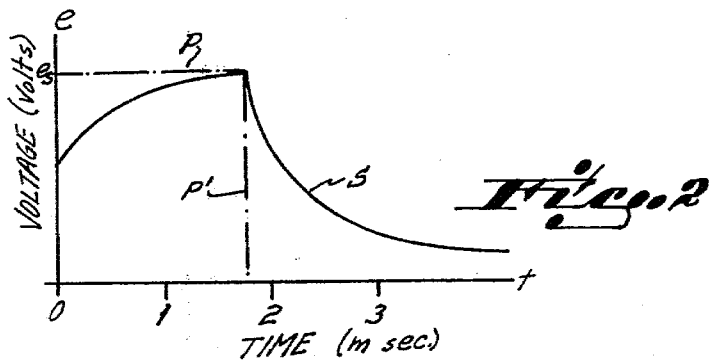
Fig. 2
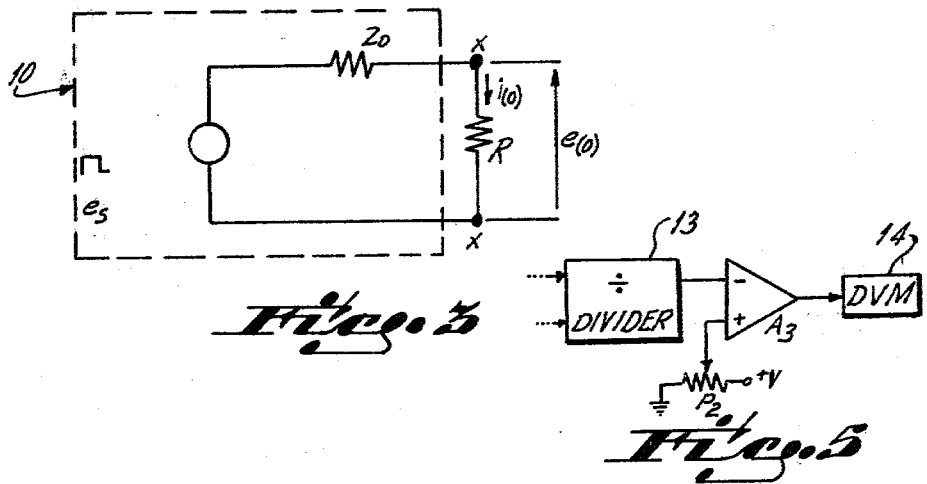
Fig. 3
Fig. 5
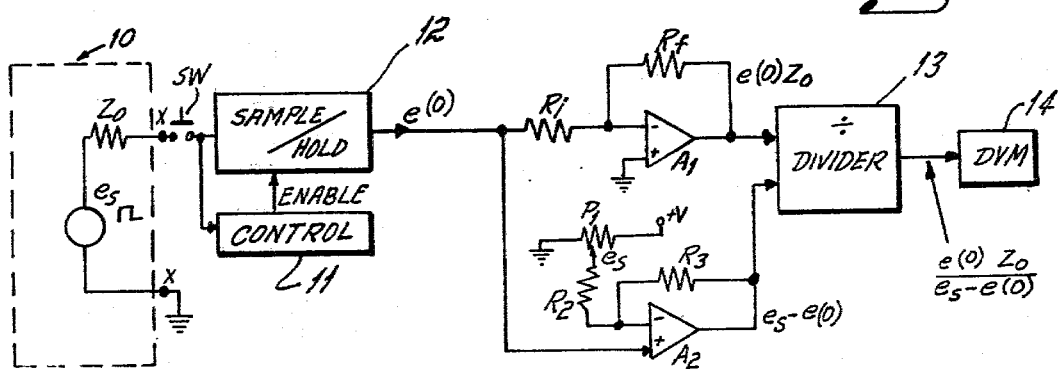
Fig. 4

METHOD AND APPARATUS FOR MEASURING THE OHMIC CONTACT RESISTANCE OF AN ELECTRODE ATTACHED TO BODY TISSUE

BACKGROUND OF THE INVENTION

The present invention relates broadly to a method and apparatus for measuring the ohmic resistance at the area of contact between body tissue and an electrode attached to the tissue. By way of illustration, the invention is directed to a method and apparatus for measuring the ohmic contact resistance between cardiac tissue and a pacemaker electrode so that the electrode can be surgically implanted in the heart at a location where the contact resistance is relatively low, thereby assuring more reliable operation of the pacemaker.

The natural atrial-ventricular stimulating system of the heart in many adults and some children is defective. In some cases, a defective natural stimulating system can be aided by a pacemaker of either the external or implantable type. A pacemaker includes miniaturized, battery-powered, self-contained pulse generator for generating pulses and an electrode for conducting the pulses to the heart. Most pacemaker pulse generators generate pulses having a fixed amplitude although the amplitude of pulses generated by some pacemaker pulse generators is adjustable. The pulses provide pacing signals for periodically stimulating the heart, thereby causing the heart to beat in the way a normal natural stimulating system causes the heart to beat. The frequency of the pulses generated by the pulse generator is preadjusted so that the pulses cause the heart to beat at a desired rate.

One known procedure for installing or replacing a pacemaker is merely to surgically implant the pacemaker electrode on as trial-and-error basis until a location is found where the pulses generated by the pacemaker pulse generator cause the heart to beat at the desired rate. Such a procedure overlooks the possibility that the resistance at the area of contact between cardiac tissue and the electrode may be relatively high at the time the electrode is implanted which in turn can mean that the initial threshold for stimulating the heart may be relatively high. The contact resistance can reasonably be expected to increase due to formation of scar tissue at the point where the electrode is implanted as the wound heals. As a result, the threshold for stimulating the heart may become even higher. Therefore, even though a pacemaker having a fixed amplitude pulse generator causes the heart to beat at the desired rate at the time the electrode is implanted, the increase in contact resistance caused by formation of the scar tissue as the wound heals may cause the threshold for stimulating the heart to become so high that the pulses generated by the pulse generator no longer cause the heart to beat. In pacemakers having adjustable amplitude pulse generators, if the initial threshold for stimulating the heart is relatively high due to relatively high resistance at the area of contact between cardiac tissue and the electrode, the amplitude of the pulses generated by the pulse generator must be adjusted upwardly until the pulses cause the heart to beat at the desired rate. However, the high voltage needed to cause the heart to beat may precipitate deterioration of cardiac tissue around the electrode which means that additional scar tissue will form even after the wound at the point where the electrode is implanted heals which in turn means that the contact resistance can reasonably be expected to increase. As a result, the threshold for stimulating the heart may become so high that the pulses generated by the pulse generator no longer cause the heart to beat.

Furthermore, high contact resistance causes greater attenuation of the natural stimulus fed back for inhibiting the pacemaker pulse generator in a demand-type pacemaker. Consequently, the pulse generator may generate a pulse even though the natural stimulating system causes the heart to beat. As a result, the pulse from the pulse generator presents the risk of inducing fibrillation which can cause death.

A more qualitative procedure for installing or replacing a pacemaker is discussed by J. W. Calvin, "Intraoperative Pacemaker Electrical Testing," *Ann. Thorac. Surg.*, Volume 26, Page 165 (1978). Calvin calculates an impedance by dividing the known pulse generator voltage by the measured current through the electrode after the threshold is set, and he reports that an acceptable range for impedance is 300–800 ohms. S. S. Barold and J. A. Winner, "Techniques and Significance of Threshold Measurements for Cardiac Pacing," *Chest*, Volume 70, Page 760 (1976), calculate the impedance by dividing the average pulse generator voltage measured on an oscilloscope by the average current through the electrode also measured on an oscilloscope. Those authors also indicate that some commercially available threshold analyzers measure the pulse generator voltage and the current through the electrode needed for calculating the impedance at an arbitrary point in time, for example, 90 microseconds, from the onset of a pulse.

Merely calculating the impedance, however, has certain drawbacks since the calculated impedance does not indicate the state of the conductive pathway which determines whether or not the pulses generated by the pulse generator cause the heart to beat. The state of the conductive pathway is determined mainly by the resistance at the area of contact between cardiac tissue and the electrode. Specifically, the threshold for stimulating the heart increases linearly with an increase in the contact resistance. Consequently, the contact resistance is the critical factor in determining whether or not the pulses generated by the pulse generator cause the heart to beat. Also, if the contact resistance is high, the natural stimulus fed back for inhibiting the pulse generator in a demand-type pacemaker may be attenuated to such an extent that the pulse generator will not be inhibited resulting in the risk of inducing fibrillation which can cause death. Therefore, the separate value of contact resistance is important in determining whether or not the location of the electrode should be changed.

SUMMARY OF THE INVENTION

The present invention provides a method and apparatus for measuring the ohmic resistance at the area of contact between body tissue and an electrode attached to the tissue, for example, cardiac tissue and a pacemaker electrode surgically implanted in the heart during installation or replacement of a pacemaker. Based on the measured contact resistance, a surgeon can select an optimum low-resistance location at which to implant the electrode in the heart, thereby assuring more reliable operation of the pacemaker.

After the electrode is surgically implanted in the heart, the pacemaker pulse generator, electrode, heart, and return path through the body to the pulse generator form an electrical circuit. In accordance with the invention, an apparatus is connected across the electrical circuit including the electrode and heart. The apparatus samples and holds the instantaneous voltage across the electrical circuit including the electrode and heart at the onset of the pulse generated by the pulse generator, at which time the effect of capacitance in the electrical circuit formed by the pacemaker, including the pulse generator and electrode, and the heart is such that the current produced is determined only by the pulse generator voltage and equivalent output impedance, the resistance of the electrode wire, and the resistance at the area of contact between cardiac tissue and the electrode. The apparatus derives the contact resistance from the instantaneous voltage based on an equivalent circuit model for the electrical circuit formed by the pacemaker and the heart taking into account the effect of capacitance at the onset of a pulse.

In accordance with a preferred embodiment of the invention, the apparatus includes control circuitry which is triggered by the leading edge of a pulse generated by the pulse generator. The control circuitry generates an enabling signal in response to the onset of the pulse.

The apparatus further includes sample and hold circuitry which is activated by the enabling signal generated by the control circuitry. In response to the enabling signal, the sample and hold circuitry captures the instantaneous voltage across the electrical circuit including the electrode and heart.

The apparatus also includes analog signal processing circuitry based on an equivalent circuit model for the electrical circuit formed by the pacemaker, including the pulse generator and electrode, and the heart taking into account the effect of capacitance at the onset of a pulse for deriving the resistance at the area of contact between cardiac tissue and the electrode from the instantaneous voltage held in the sample and hold circuitry. The apparatus also includes a device for displaying the measured contact resistance so that a surgeon can determine whether or not to surgically implant the electrode at another location on the heart in order to assure that the contact resistance is relatively low so that there is a higher probability that the pacemaker will continue to cause the heart to beat for a longer time after the electrode is implanted and also so that attenuation of the natural stimulus fed back for inhibiting the pulse generator in a demand-type pacemaker is relatively low for minimizing the risk of inducing fibrillation.

BRIEF DESCRIPTION OF THE DRAWING

The contact resistance measuring device of the invention will be better understood and the advantages thereof will be better appreciated after a consideration of the description given below in connection with the drawing. In the drawing:

FIG. 1 is a diagram of an equivalent circuit model for the electrical circuit formed by a pacemaker, including the pacemaker pulse generator and the pacemaker electrode, and the heart;

FIG. 2 is a plot of the voltage response characteristic of the electrical circuit formed by the pacemaker and the heart as represented by the equivalent circuit model in FIG. 1 superimposed on a pulse generated by the pulse generator;

FIG. 3 is a diagram of the equivalent circuit model in FIG. 1 at the onset of a pulse generated by the pulse generator;

FIG. 4 is a schematic circuit diagram of an apparatus in accordance with a preferred embodiment of the invention for determining the contact resistance where the resistance of the electrode wire is small relative to the contact resistance; and FIG. 5 illustrates a modification of the circuit shown in FIG. 4 for determining the contact resistance where the resistance of the electrode wire is not small relative to the contact resistance.

DETAILED DESCRIPTION

The electrical circuit formed by a pacemaker, comprising the pacemaker pulse generator and the pacemaker electrode, and the heart is a resistive-capacitive network which includes the resistance at the area of contact between cardiac tissue and the electrode. An equivalent circuit model for the electrical circuit formed by the pacemaker and the heart is shown in FIG. 1.

With reference to FIG. 1, the pacemaker pulse generator 10 is represented by a voltage source for generating pulses having an amplitude $e_s$ in series with an equivalent output impedance $Z_0$. The resistance of the electrode wire plus the contact resistance between cardiac tissue and the electrode is indicated by a purely ohmic resistance R. The heart is represented by a resistance $R_s$ and a capacitance $C_s$ in a series circuit. $R_p$ and $C_p$ are the resistive and capacitive components of a parallel circuit representing body tissue surrounding the electrode constituting the body return path. e represents the instantaneous voltage applied through the electrode to the heart.

The pulses generated by pulse generator 10 are substantially rectangular, such as the pulse P in FIG. 2, and could have a duration of 1.7 milliseconds, for example. The instantaneous voltage e depends in part on the value of output impedance $Z_0$ of pulse generator 10. If the impedance of the pulse generator is low, the voltage e is substantially rectangular. If the impedance of the pulse generator is large, the voltage e has a shape as shown by the pacing signal S in FIG. 2 which is similar in shape to the pacing signal produced by the natural stimulating system. Consequently, a pulse generator with a large output impedance, such as Medtronic Model 5880A, manufactured by Medtronic, Inc. of Minneapolis, Minnesota, is preferably used so that the artificially produced stimulus approximates a naturally occurring stimulus.

The rise time of the pulse P is insignificant. Consequently, the leading edge P' of the pulse P approximately coincides with the voltage axis in FIG. 2 at the onset of the pulse.

As shown in FIG. 1, an instantaneous current i flows through the electrode whenever the pulse generator generates a pulse. The current i divides into three currents, $i_1$, $i_2$, and $i_3$, flowing into the three branches of the electrical circuit including the heart and surrounding body tissue. Specifically, the current $i_1$ flows through surrounding body tissue resistance $R_p$, the current $i_2$ flows into surrounding body tissue capacitance $C_p$, and the current $i_3$ flows through the series circuit formed by resistance $R_s$ and capacitance $C_s$ comprising the impedance of the heart, the current i being equal to the sum of the currents $i_1$, $i_2$, and $i_3$.

If one were to measure average values for the voltage e and the current i, the resulting ratio e/i would yield some impedance relating to the entire electrical circuit formed by the pacemaker and the heart. However, the contact resistance cannot be separately determined from the calculated impedance, since the impedance indicates only the combined effect of electrode resistance R, surrounding body tissue resistance $R_p$ and capacitance $C_p$, and heart resistance $R_s$ and capacitance $C_s$. Consequently, determining whether or not the electrode should be surgically implanted at a different location on the heart in order to avoid high contact resistance would not be possible.

In accordance with the invention, the contact resistance is derived based on the equivalent circuit model in FIG. 1 for the electrical circuit formed by the pacemaker and the heart taking into account the principle of conservation of energy that voltage across a capacitor cannot change instantaneously. Therefore, at the onset of a pulse generated by the pulse generator, surrounding body tissue capacitance $C_p$ is fully discharged and effectively acts as a short circuit across both surrounding body tissue resistance $R_p$ and the circuit of the heart formed by resistance $R_s$ and capacitance $C_s$. As a result, the circuit in FIG. 1 at the onset of a pulse simplifies to the equivalent circuit model shown in FIG. 3.

At the onset of a pulse, current i(0) in FIG. 3 is given by Equations I and II below.

$$i(0) = e_s/[Z_0+R] \quad \text{(Equation I)}$$

$$i(0) = e(0)/R \quad \text{(Equation II)}$$

By substituting the right side of Equation II for the current i(0) into Equation I and solving Equation I for the value of electrode resistance R, the following Equation III results.

$$R = (e(0)Z_0/[e_s - e(0)]) \quad \text{(Equation III)}$$

As can be seen from Equation III, electrode resistance R can be determined if the pulse amplitude $e_s$ and output impedance $Z_0$ as well as the instantaneous voltage e(0) are known or measured.

A preferred embodiment of an apparatus in accordance with the invention for determining the contact resistance will now be described. Basically, the apparatus comprises circuitry for capturing the voltage e(0) at the onset of a pulse generated by the pulse generator and circuitry for solving Equation III based on known values for $e_s$ and $Z_0$ and the measured value for e(0). The values for the pulse amplitude $e_s$ and output impedance $Z_0$ are listed on the pulse generator nameplate or can be readily determined from Thevenin's equivalent circuit.

The apparatus for deriving the contact resistance includes control circuitry responsive to the leading edge of a pulse generated by the pulse generator for enabling sample and hold circuitry for storing the instantaneous voltage e(0) and analog signal processing circuitry for solving Equation III. The block diagram of the apparatus is shown in FIG. 4. The apparatus is connected to the terminals X—X in FIG. 1 across the electrical circuit including the electrode and heart.

As shown in FIG. 4, a switch SW is first closed. Switch SW connects control circuitry 11 to the terminals X—X. Control circuitry 11 is triggered by the rising voltage occurring at the leading edge of a pulse generated by the pulse generator. Control circuitry 11 generates an enabling signal in response to the onset of the pulse for enabling sample and hold circuitry 12. In response to the enabling signal generated by the control circuitry 11, sample and hold circuitry 12 captures the instantaneous voltage across the terminals X—X. As mentioned earlier, the rise time of the pulse P in FIG. 2 is insignificant. Preferably, control circuitry 11 and sample and hold circuitry 12 are commercially available and are selected for capturing and storing the instantaneous voltage within an extremely short time, on the order of 500 nanoseconds or less, from the onset of a pulse generated by the pulse generator. The instantaneous voltage should be captured and stored in preferably less than two microseconds and not more than five microseconds from the onset of the pulse generated by the pulse generator. The stored instantaneous voltage corresponds to the voltage e(0) in FIG. 3 across the electrode resistance R.

The output of sample and hold circuitry 12 is connected to amplifiers $A_1$ and $A_2$ as shown in FIG. 4 so that the stored instantaneous voltage e(0) is applied to the amplifiers $A_1$ and $A_2$. Amplifier $A_1$ is an inverting amplifier with an input resistor $R_i$ and a feedback resistor $R_f$ adjusted for a gain $R_f/R_i$ equal to the value of the known output impedance $Z_0$ of the pulse generator. Consequently, the signal at the output of amplifier $A_1$ is $$e(0)Z_0 \quad \text{(Equation IV)}$$

Amplifier $A_2$ is a noninverting amplifier with an offset adjusted by means of a potentiometer $P_1$ to equal the pulse amplitude $e_s$. The values of resistors $R_2$ and $R_3$ are selected for a gain $R_3/R_2$ equal to one. Consequently, the signal at the output of amplifier $A_2$ is $$e_s - e(0) \quad \text{(Equation V)}$$

The outputs of amplifiers $A_1$ and $A_2$ are connected to a divider 13. Divider 13 divides the signal at the output of amplifier $A_1$ which has a value $e(0)Z_0$ by the signal at the output of amplifier $A_2$ which has a value $e_s - e(0)$, thereby producing a signal equal to the value of the electrode resistance R in accordance with Equation III.

The known value of the equivalent output impedance $Z_0$ of the pulse generator enables the gain $R_f/R_i$ of amplifier $A_1$ in FIG. 4 to be preset. The Medtronic Model 5880A pulse generator mentioned above has an output impedance $Z_0$ equal to 4.84 kilohms, for example. Furthermore, the known value of the pulse amplitude $e_s$ enables the offset of amplifier $A_2$ to be preset by means of potentiometer $P_1$. For example, the Medtronic Model 5880A pulse generator mentioned above has a pulse amplitude $e_s$ equal to 31 volts. Once the gain $R_f/R_i$ of amplifier $A_1$ and the offset of amplifier $A_2$ are preset, the circuitry is ready for deriving the electrode resistance from the instantaneous voltage e(0) stored in sample and hold circuitry 12.

The resistance of the electrode wire varies from one commercially available electrode to another. Generally, the resistance of the electrode wire ranges from 6–75 ohms. The Medtronic Sutureless Myocardial Lead Model 6917 electrode, for example, has a wire resistance of six ohms. In contrast, measured resistance at the area of contact between cardiac tissue and a pacemaker electrode surgically implanted in the heart ranges upwardly from a minimum of about 150–160 ohms. When the resistance of the electrode wire is small, such as six ohms, the resistance of the electrode wire is insignificant relative to the contact resistance and, after the contact resistance reaches a certain value, may even fall within the error inherent in the operation of the circuitry. Consequently, the resistance of the electrode wire can be ignored, and, as shown in FIG. 4, the output of divider 13 can be connected to a digital voltmeter 14 which, in a practical sense, displays the measured contact resistance in ohms.

If the resistance of the electrode wire is not small, that is, if the resistance of the electrode wire is on the order of 75 ohms, the resistance of the electrode wire is not insignificant relative to the contact resistance and must be subtracted in order to obtain a measurement of contact resistance. A circuit modification of FIG. 4 for subtracting the resistance of the electrode wire is shown in FIG. 5. As shown in FIG. 5, the output of divider 13 is not connected directly to digital voltmeter 14. Instead, the output of divider 13 is connected to one input of an amplifier $A_3$. The other input of amplifier $A_3$ is connected to a potentiometer $P_2$ which can be adjusted to a voltage having a magnitude equal to the magnitude of the resistance of the electrode wire. Preferably, however, the electrode is first connected directly across the pulse generator, and then potentiometer $P_2$ is adjusted to null the signal at the output of amplifier $A_3$ immediately before the electrode is implanted in the heart. Such a procedure not only results in providing for automatically subtracting the resistance of the electrode wire but also for nulling errors inherent in the operation of the circuitry. The output of amplifier $A_3$ is connected to digital voltmeter 14. Amplifier $A_3$ automatically subtracts the resistance of the electrode wire so that the actual contact resistance is displayed by digital voltmeter 14.

For an individual electrode, the threshold required for stimulating the heart increases linearly with an increase in contact resistance. Consequently, the contact resistance is a critical factor in determining the optimum location on the heart to implant the electrode. When the pacemaker electrode is surgically implanted in the heart, an assessment of the contact resistance provides a better procedure for evaluating whether or not the electrode is implanted at a desirable location.

Based on the measured contact resistance, a surgeon can determine whether or not to surgically implant the electrode at another location on the heart in order to assure that the contact resistance is relatively low so that there is a higher probability that the pacemaker will continue to cause the heart to beat for a longer time after the electrode is implanted. Also, in a demand-type pacemaker, if the contact resistance is relatively high, the natural stimulus fed back for inhibiting the pulse generator may be attenuated to such an extent that the pacemaker will not be inhibited so that there is a risk the pulse generator will generate a pulse causing fibrillation possibly resulting in death. By measuring the contact resistance, a decision can be made whether or not to relocate the electrode on the heart in an area of lower contact resistance to minimize the risk that fibrillation might occur.

In summary, the invention provides a method and apparatus based on the dynamic behavior of the electrical circuit formed by the pacemaker and the heart at the onset of a pulse generated by the pulse generator for measuring the ohmic resistance at the area of contact between cardiac tissue and the electrode and immediately displaying the measured contact resistance. The advantages of determining contact resistance in accordance with the invention are numerous. By knowing the contact resistance, a surgeon can then appraise whether the threshold for pacing the heart is due primarily to contact resistance or the distance of the electrode from the Purkinje fibers in the heart. The procedure, therefore, provides a standard approach for determining whether or not to surgically implant the electrode at a different location on the heart during installation or replacement of a pacemaker. The contact resistance is measured instantaneously, and there is no need for hand calculations. No measurement of current is required. The apparatus can be battery-powered and may be combined with a threshold analyzer with digital readout of the measured contact resistance in ohms. The apparatus is economical and easily constructed. In addition, the value of contact resistance can be used to calculate the actual voltage applied to the heart which may prove to be of great value in future research.

The method and apparatus for measuring the contact resistance of a pacemaker electrode surgically implanted in the heart has been described in connection with the drawing which shows various embodiments for carrying out the invention. However, other modifications may become evident to those of skill in the art without departing from the spirit and scope of the invention.

Illustration of the invention in connection with measuring the ohmic resistance at the area of contact between cardiac tissue and a pacemaker electrode surgically implanted in the heart is by way of illustration and not by way of limitation. That is, the invention relates broadly to measuring the ohmic contact resistance of an electrode attached to body tissue and not just to measuring the ohmic contact resistance of a pacemaker electrode implanted in the heart. For example, the invention can be used for measuring the ohmic resistance at the area of contact between diaphragm tissue and a pacemaker electrode surgically implanted in the diaphragm or the ohmic contact resistance of an electrode attached to other body tissue as in the case of an electrode attached to the skin, such as an electrocardiograph electrode. Such a result is due to the effect of the surrounding body tissue capacitance which enables measuring the ohmic contact resistance of an electrode attached to body tissue based on the equivalent circuit model shown in FIG. 3. In order to ascertain the true scope of the invention, reference must be had to the appended claims.

We claim:

1. A method for measuring the ohmic contact resistance of an electrode attached to body tissue, the method including the steps of:
    attaching the electrode to the body tissue;
    connecting a pulse generator having a given pulse amplitude and a given equivalent output impedance to the electrode, the pulse generator, electrode, and body tissue forming an electrical circuit;
    generating a pulse by means of the pulse generator;
    determining the instantaneous voltage across the body tissue and electrode at the onset of the pulse;
    deriving the ohmic contact resistance of the electrode based on the given amplitude, the given equivalent output impedance, and the instantaneous voltage; and
    displaying the ohmic contact resistance.

2. A method for measuring the ohmic contact resistance of an electrode surgically implanted in a patient's heart, the electrode for electrically connecting a pacemaker pulse generator having a given equivalent output impedance to the heart, the pulse generator, electrode, and heart forming an electrical circuit, the pulse generator for generating discrete pulses having a given amplitude, the pulses for providing pacing signals for stimulating the heart, the method including the steps of:
generating an enabling signal in response to the leading edge of a pulse;
sampling and holding the instantaneous voltage across the electrode and heart in response to the enabling signal;
deriving the ohmic contact resistance of the electrode based on the given equivalent output impedance, the given amplitude, and the instantaneous voltage; and
displaying the ohmic contact resistance.

3. Apparatus for measuring the ohmic contact resistance of an electrode attached to body tissue, said apparatus comprising:
a pulse generator connected to said electrode, said pulse generator having a given pulse amplitude and a given equivalent output impedance, said pulse generator, electrode, and body tissue forming an electrical circuit;
a means connected across said body tissue and electrode for determining the instantaneous voltage across said body tissue and electrode at the onset of a pulse generated by said pulse generator;
analog signal processing circuitry connected to said instantaneous voltage determining means for deriving the ohmic contact resistance of said electrode based on said given amplitude, said given equivalent output impedance, and said instantaneous voltage; and
a means connected to said analog signal processing circuitry for displaying said ohmic contact resistance derived by said signal processing circuitry.

4. Apparatus for measuring the ohmic contact resistance of an electrode surgically implanted in a patient's heart, said electrode for electrically connecting a pacemaker pulse generator having a given equivalent output impedance to said heart, said pulse generator, electrode, and heart forming an electrical circuit, said pulse generator for generating discrete pulses having a given amplitude, said pulses for providing pacing signals for stimulating said heart, said apparatus comprising:
control circuitry connected to said pulse generator and responsive to the leading edge of a pulse for generating an enabling signal;
sample and hold circuitry connected across said electrode and heart and connected to said control circuitry and responsive to said enabling signal for capturing the instantaneous voltage across said electrode and heart at the onset of said pulse;
analog signal processing circuitry connected to said sample and hold circuitry and responsive to said captured instantaneous voltage for deriving the ohmic contact resistance of said electrode based on said given equivalent output impedance, said given amplitude, and said captured instantaneous voltage; and
a means connected to said analog signal processing circuitry for displaying said ohmic contact resistance derived by said analog signal processing circuitry.

5. The apparatus in claim 3 or 4 wherein said equivalent output impedance of said pacemaker is $Z_0$ and said amplitude of said pulses is $e_s$ and wherein said analog signal processing circuitry includes:
an inverting amplifier having an input and an output, said inverting amplifier input being connected by an input resistor to said sample and hold circuitry, said inverting amplifier input and output being interconnected by a feedback resistor, the ratio of said feedback resistor to said input resistor being preset to equal $|Z_0|$;
a noninverting amplifier having an input and an output, said noninverting amplifier input being connected to said sample and hold circuitry;
circuitry for producing an offset in the signal at said noninverting amplifier output, said offset being preset to equal $e_s$; and
a divider having two inputs and an output, said divider inputs being respectively connected to said amplifier outputs for dividing the signal at said inverting amplifier output by the signal at said noninverting amplifier output.

6. The apparatus in claim 5 wherein the electrode wire resistance is small relative to said ohmic contact resistance and said divider output is connected to said display means.

7. The apparatus in claim 5 wherein the electrode wire resistance is not small relative to said ohmic contact resistance and wherein said analog signal processing circuitry further includes:
a second noninverting amplifier having an input and an output, said noninverting amplifier input being connected to said divider output;
circuitry for producing an offset in the signal at said second noninverting amplifier output, said offset being preset to equal said electrode wire resistance, said second noninverting amplifier output being connected to said display means.

8. The apparatus in claim 6 wherein said display means is a digital voltmeter.

9. The apparatus in claim 7 wherein said display means is a digital voltmeter.

* * * * *